United States Patent [19]
Roncucci et al.

[11] Patent Number: 5,965,598
[45] Date of Patent: Oct. 12, 1999

[54] ZINC-PHTHALOCYANINES AND CORRESPONDING CONJUGATES, THEIR PREPARATION AND USE IN PHOTODYNAMIC THERAPY AND AS DIAGNOSTIC AGENTS

[75] Inventors: Gabrio Roncucci, Loc. Mensanello; Donata Dei, San Gittignano; Maria Paola De Filippis, Taranto; Lia Fantetti, Florence; Ilaria Masini, Florence; Barbara Cosimelli, Florence; Giulio Jori, Padua, all of Italy

[73] Assignee: Molteni L. & C. dei Fratelli Alitti Societa di esercizio S.p.A., Italy

[21] Appl. No.: 09/133,618

[22] Filed: Aug. 13, 1998

[30] Foreign Application Priority Data

Aug. 14, 1997 [IT] Italy .................................. MI97A1940

[51] Int. Cl.$^6$ ......................... A61K 31/40; C07D 487/22
[52] U.S. Cl. ......................... 514/410; 514/183; 514/185; 540/133; 540/124; 540/125; 540/126; 540/139; 540/140
[58] Field of Search ..................................... 540/139, 140, 540/122, 123, 124, 125, 127; 514/185, 410

[56] References Cited

U.S. PATENT DOCUMENTS

| | | | |
|---|---|---|---|
| 5,073,295 | 12/1991 | Bruttel et al. | 252/301.19 |
| 5,192,788 | 3/1993 | Dixon et al. | 514/410 |
| 5,281,616 | 1/1994 | Dixon et al. | 514/410 |
| 5,427,616 | 6/1995 | Tsuji et al. | 106/412 |
| 5,446,141 | 8/1995 | Itoh et al. | 540/139 |

OTHER PUBLICATIONS

European Search Report, Berlin, Dec. 17, 1998, Examiner Siatou, E.
J. Photochem. & Photobio., vol. 51, No. 3, 1990, pp. 351–356, D. Wohle, "Synthesis of positively charges phthalocyanines and their activity in the photodynamic therapy of cancer cells".
J. Photochem. & Photobio., vol. 32, No. 3, Feb. 1996, pp. 159–164, Minnock A et al. "Photoinactivation of Bacteria. Use of a Cationic Water–Soluble Zinc Phthalocyanine to Photoinactive both Gram–Negative and Gram–Positive Bacteria".
J. Photochem. * Photobio., vol. 37, No. 3, Feb. 1997, pp. 219–229, H. Dummin et al., "Selective photosensitization of mitochondria in HeLa cells by cationic Zn(II) phthalocyanines with lipophilic side chains".
Tetrahedron Letter, vol. 23, No. 30, 1982, pp. 3023–3026, C.C. Leznoff et al., "The Synthesis of a soluble, unsymmetrical phthalocyanine on a polymer support".
Dyes and Pigments, vol. 33, No. 1, Jan. 1997, pp. 65–78, Griffiths, J. et al., "Some Observations on the Synthesis of Polysubstituted Zinc Phthalocyanine Sensitisers for Photodynamic Therapy".
Patent Abstracts of Japan, vol. 97, No. 7, Jul. 31, 1997.
J. Photochem. & Photobio., vol. 65(3), 1997, pp. 397–402, Wood et al., "The Subcellular Localization of Zn(II)–Phthalocyanines and Their Exposure to Light".

J. Photochem. * Photobio., vol. 6, 1990, pp. 121–132, Rousseau et al., Biological Activities of Phthalocyanines XII+ Synthesis Tumor Uptake and Biodistribution of $^{14}$C–LAbeled Disulfonated and Trisulfonated Gallium Phthalogyanine in C3H Mice.
British Journal of Cancer, vol. 74, 1891–1899, C. Ometto et al., "Tumour–localising and –Photosensitising properties of a novel zinc(II) octadecylphthalocyanine".
SPIE, vol. 2078, 1993, pp. 106–118, Giulio Jori et al., "Photodynamic Therapy of Cancer".
Br. J. Surg., vol. 77, Jan. 1990, pp. 93–96, H. Barr et al. "Photodynamic Therapy for Colorectal Cancer: a quantitative pilot study".
J. Photochem. & Photobio., vol. 37, 1997, pp. 219–229, H. Dummin et al., "Selective Photosensitization of mitochondria in HeLa cells by cationic Zn(II)phthalocyanines with lipophilic side–chains".
Dyes and Pigments, vol. 18, 1992, pp. 91–102, Wohrle et al., "Efficient Synthesis of Phthalocyanines and Related Macrocyclic Compounds in the Presence of Organic Bases".
J. Photochem. & Photobio., vol. 36, 1996, pp. 87–93, Giulio Jori, "Tumour Photosensitizers: approaches to enchance the selectivity and efficiency of photocynamic therapy".
J. Photochem. & Photobio., vol. 49, No. 3, 1989, pp. pp. 279–284, C.C. Leznoff et al., "Synthesis and Photocytotoxicity of some new substituted phthalocyanines".
Seminars in Hematology, vol. 26, No. 1, Jan. 1989, pp. 27–34, Charles J. Gomer, "Photodynamic Therapy in the Treatment of Malignancies".
Int. J. Radiat. Biol., vol. 47, No. 2, 1985, pp. 145–147, Ehud Ben–Hur et al., "The phthalocyamins: a new class of mammalian cells photosensitizers with a potential for cancer phototherapy".
Rosenthal et al., Chem. Abst. vol. 108, 1988 108: 127680a.

Primary Examiner—Mukund Shah
Assistant Examiner—Pavanaram K Sripada
Attorney, Agent, or Firm—Hedman, Gibson & Costigan, P.C.

[57] ABSTRACT

The present invention refers to zinc-phthalocyanines of general formula (I)

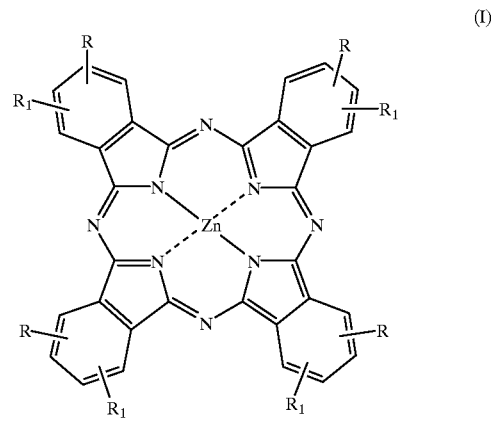

(I)

to processes for their preparation and to their use as phototherapeutic and photodiagnostic agents as free molecules and as conjugates with macromolecular carrier molecules.

20 Claims, No Drawings

ZINC-PHTHALOCYANINES AND CORRESPONDING CONJUGATES, THEIR PREPARATION AND USE IN PHOTODYNAMIC THERAPY AND AS DIAGNOSTIC AGENTS

SCOPE OF INVENTION

The present invention refers to zinc-phthalocyanines of general formula (I)

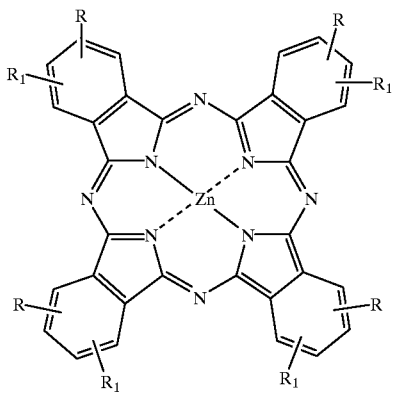

(I)

in which:

R and $R_1$, same or different from one another, represent H or the group $X\text{-}R_5$, where:

X is chosen in the group consisting of —$CH_2$—, O, N, S, C=O, and

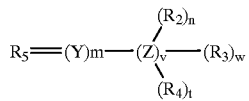

where:

Y is chosen in the group consisting of $C_{1-10}$-alkyl, phenyl possibly substituted, $(CH_2CH_2O)_p$, where p ranges from 1 to 4;

Z is chosen in the group consisting of H, N, O S, $SO_3$, —CH—, —$CH_2$— carbon atom, $CH_2O$, CONH, $(CH_2)_qCO_2$, where q ranges from 0 to 2;

v is an integer comprised between 1 and 5

$R_2$ is chosen in the group consisting of H, $C_{1-6}$-alkyl, $PO(OEt)_2$, $CH_2CH_2NH_2$, aryl, and crown ether, or it forms, with the Z group to which it is bound, a saturated or unsaturated heterocycle, possibly substituted, which may contain up to two heteroatoms chosen in the group consisting of: N, O and S;

$R_3$ and $R_4$, which may be the same or different from one another, are chosen in the group consisting of H, $CH_3$, and $C_2H_5$;

m, n, w, t (independently from one another) are 0 or 1;

with the proviso that at least one of R and $R_1$ is always other than H.

These products show high photodynamic properties and a marked absorption in the red region of the visible spectrum. These compounds are useful both as such as in the form of conjugates with macromolecular carriers, in the treatment of infectious diseases and diseases characterized by cellular hyperproliferation, and in particular tumours, psoriasis, atheromas, intimal hyperplasia, benign prostate hyperplasia, or else for diagnostic purposes.

STATE OF THE ART

It is known that, once organic molecules containing the chromofluorophore macrocycle of the phthalocyanine are photo-activated by irradiation with visible light, they are capable of generating hyper-reactive derivatives of oxygen, above all singlet-oxygen or radicals, which are characterized by a high degree of cytotoxicity, and hence are potentially interesting for therapeutic applications, such as photodynamic therapy (PDT), and/or diagnostic applications (E. Ben-Hur and I. Rosenthal, Int. J. Radiat. Biol., 47 145–147 (1985)).

The therapeutic application of photosensitizing molecules, prevalently studied in connection with their anti-cancer activity, is based upon the use of photosensitizing agents of a porphyrin nature (Gomer C. J., Seminars in Hematology, Vol. 26, pp. 27–34, 1989), which, albeit giving promising results in the curative or palliative treatment of various neoplasms, are markedly limited by the low photosensitization efficiency, poor selectivity, and prolonged persistence in the skin, which may often cause phenomena of generalized photosensitivity (Jori G., J. Photochem. Photobiol., B: Biol., Vol. 36, pp. 87–93, 1996).

For photosensitizing agents to be usefully employed for therapeutic and/or diagnostic purposes in vivo, the following properties are indispensable:

i) low dark toxicity with a high production of hyperactive derivatives of oxygen, above all singlet-oxygen or radicals, or have a high fluorescence quantum yield;

ii) selective accumulation by the cells that are responsible for a given pathological condition and fast elimination from the tissues that are not affected by the said pathological condition;

iii) capacity of being activated by radiation of high wavelength that is able to penetrate more deeply into the tissues as compared with radiation of shorter wavelength;

iv) possibility of being conjugated to macromolecular carriers, albeit maintaining the characteristics of photosensitization efficiency.

Thus it is evident how important it is, for therapeutic and/or diagnostic purposes, to be able to develop compounds which, while maintaining the necessary specific biocidal properties, have the characteristics specified above.

Notwithstanding the advantages that may be foreseen for molecules belonging to the class of the phthalocyanines and possessing their basic chemical structure, only a few of these molecules have been actually assessed as potential agents for photodynamic therapy both on cell lines and in vivo at a preclinical level.

Derivatives that may fall within structure (I) presenting hydroxyl, amine or quaternary ammonium substituents have in fact been described for photosensitization of cancer cells by Leznoff C. C. et al. in "Synthesis and photocytotoxicity of some new substituted phthalocyanines", Photochemistry and Photobiology, Vol. 49, No. 3, pp. 279–284 (1989), by Wohrle D. et al. in "Synthesis of positively charged phthalocyanines and their activity in the photodynamic therapy of cancer cells", Photochemistry and Photobiology, Vol. 51, No. 3, pp. 351–356 (1990), again by Wohrle D. et al. in "Efficient synthesis of phthalocyanines and related macrocyclic compounds in the presence of organic base", Dyes and Pigments, Vol. 18, pp. 91–102 (1992), and by Dummin H. in "Selective photosensitization of mitochondria in HeLa cells by cationic Zn(II) phthalocyanines with lipophilic side-chains", J. Photochem. Photobiol., 37(3) 219–29 (1997).

Experiments of cancer phototherapy with phthalocyanines on laboratory animals have been reported by Barr H. et al. in "Photodynamic Therapy for Colorectal Cancer: a quantitative pilot study", Br. J. Surg., Vol. 77, pp. 93–96, 1990, by Schieweck K. et al. in "Liposome-delivered Zn-phthalocyanine as a phototherapeutic agent for tumours", Proc. SPIE, Vol. 2078, pp. 107–118, 1994, Ometto C. et al. in "Tumour-localizing and photosensitizing properties of a novel phthalocyanine", Br. J. Cancer, Vol. 74, pp. 1891–1899, 1996, and by Rousseau J. et al. in "Synthesis, tumour uptake and biodistribution of C14-labeled di- and tri-sulfonated gallium phthalocyanine", J. Photochem. Photobiol., B: Biol., Vol. 6, pp. 121–132, 1990.

Minnoch et al. (J. Photochem. and Photobiol., Vol. 32, No. 3, pp. 159–164, 1996) and Brown S. et al. (Photochem. and Photobiol., 65(3) pp., 1967) have described the in vitro activity of four phthalocyanine derivatives both on microorganisms and on cell lines. However, the quaternary ammonium compound which is reported as being the only one active in the series of molecules synthesized and assessed against Gram-negative and Gram-positive bacteria, consists of a mixture of compounds having different number of substituents on the phthalocyanine-moiety, and hence is not a compound defined by a precise structural identity (Griffith J. et al., Dyes & Pigments, 33(1) 65 (1997)) unlike the products described in the present invention.

DETAILED DESCRIPTION OF THE INVENTION

The present invention makes it possible to meet the above mentioned requirements by means of zinc-phthalocyanines of general formula (I) as defined previously.

These compounds present a considerable photosensitizing activity which enables them to be used in PDT of tumoral forms and other illnesses characterized by cellular hyperproliferation, but also against viral, fungal or bacterial diseases; moreover, in so far as they are fluorophores, they may be used as diagnostic agents for the identification of areas that are pathologically affected.

The presence of the substituents indicated, preferably of a hydrophilic nature, and/or the conjugation to hydrophilic carriers, can, among other things, accelerate the metabolism of the molecule, enabling a fast in vivo elimination of the chromophore, and thus preventing the onset of cutaneous phototoxicity.

According to the invention, by $C_{1-10}$-alkyl group the following are meant: methyl, ethyl, propyl, isopropyl, butyl, pentyl, hexyl, heptyl, octyl, nonyl, and decyl.

By saturated or unsaturated heterocycle possibly substituted, as defined in the general formula, the following are preferably meant: morpholine, piperidine, pyridine, pyrimidine, piperazine, pyrrolidine, and pyrroline.

According to the invention, the preferred products are those in which the group $X-R_5$ is represented by:

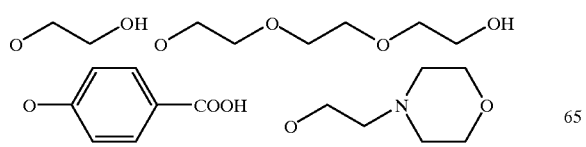

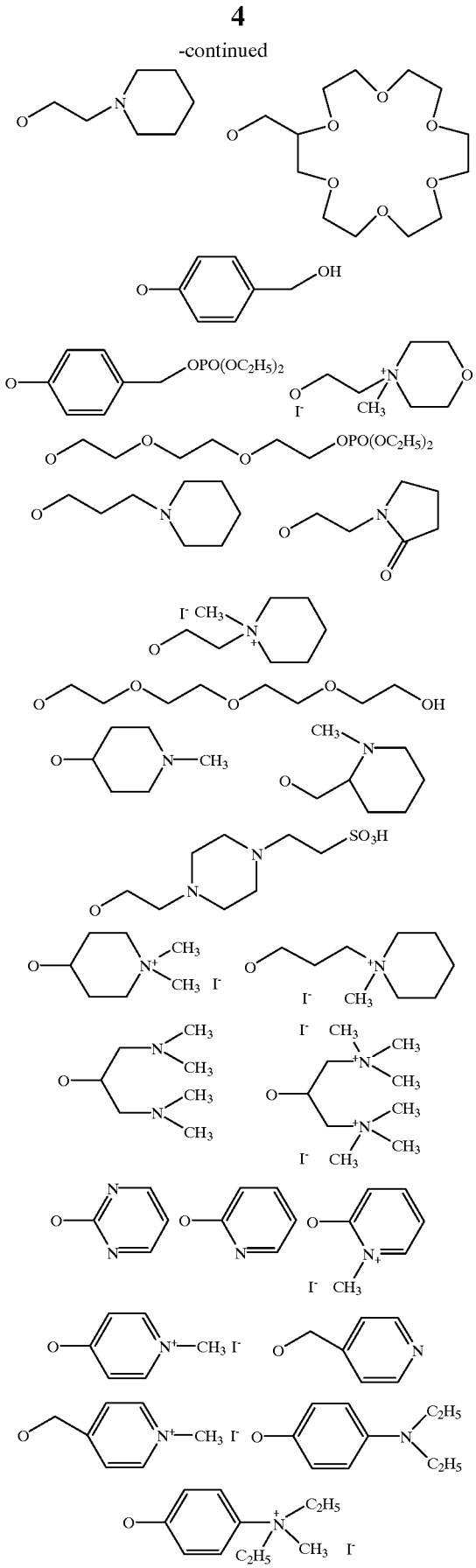

-continued

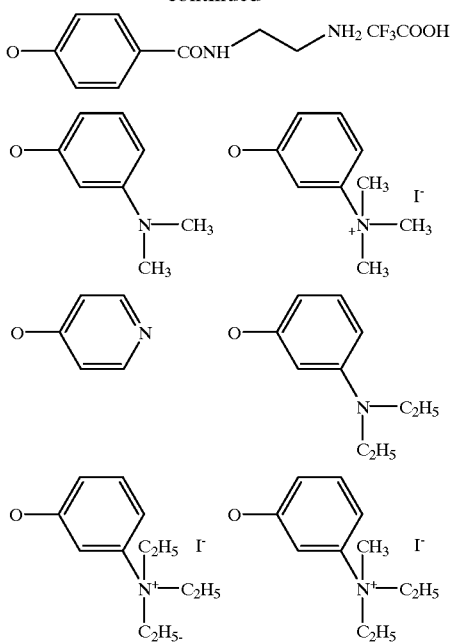

In particular, the products in which the group X-R$_5$, as specified above, contains substituents bearing tertiary or quaternary nitrogen are preferred.

Still more preferred are the compounds of formula I wherein the group X-R$_5$ is a group of formula

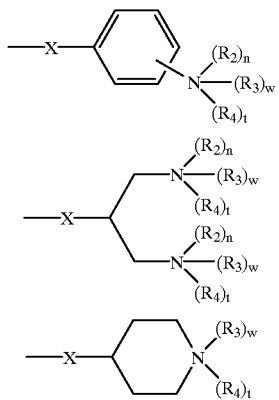

The new synthesized products have high molar extinction coefficients, a characteristic that enables the possibility of an effective therapeutic response at low dosages of active compound and show an unusually high values of the singlet oxygen quantum yields.

These products may be activated by tissue penetrating radiation having a wavelength of over 650 nm, and hence are suitable for the PDT of various deseases, both dermatological and internal.

Normally the present compounds are hydrophilic, if not they can be easily transformed into hydrophylic derivatives by conjugation with hydrophylic macromolecular carriers and are not aggregate in water solution. The products formed by photobleaching of those compounds are non toxic. This finding reinforces their usefulness as therapeutics since after having expleted their action the compounds are inactivated by the light and then no more potentially toxic in vivo.

It must be remembered that the photodynamic activity in some cases and for same substituents is exerted even at low oxygen concentration, this finding enable the use of such derivatives for the specific treatment of anaerobic microorganisms or the treatment of tumor deseases known to be characterized by an hypoxic environment.

The activity as photosensitizers, the wavelenght absorption shifted towards the red and their fluorescence, makes these molecules particularly interesting for use in photodynamic therapy and as tracers for in vivo diagnostics.

The compounds of the present invention can be prepared, in the homogenous phase, according to reaction schemes that are known in organic chemistry. The preparation of phthalocyanines was carried out via tetramerization (see Scheme 4) of the corresponding phthalonitrile of formula (II)

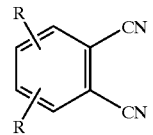

(II)

where the substituents R and R$_1$ are as defined above, using procedures that are known in the literature (Phthalocyanines—Properties and Applications, Vol. 1–4, C. C. Leznoff and A. B. P. Lever VCH Ed.).

Described in the literature are reactions of synthesis of phthalocyanines having one substituent different from the other three, starting from a dinitrile bound to the solid phase with a dinitrile differently substituted, after prior transformation into diaminoisoindolyl derivatives [Tetrahedron Letters, 23(30) 3023–3026 (1982); J. Org. Chem., 56, 82–90 (1991)].

We have surprisingly found that, following the procedure described in Example 7, also phthalocyanines of formula (I) having four identical substituents may be obtained in heterogeneous phase using polystyrene-based matrices. The condensation between one another of the dinitriles bound to the resin takes place also in the presence of a considerable excess of the dinitrile, variously substituted, in the solution, unlike what is reported in the literature.

Schemes 1–3 illustrate, as non-limiting examples, three different procedures that make it possible to obtain 3-, 4-, 4,5 and 3,6-substituted phthalonitriles, respectively.

Scheme 1 refers to the particular case in which:
R=H
R$_1$=O—R$_5$.
Schemes 2 and 3 refers to the case in which:
R=R$_1$=O—R$_5$.

As may be seen in the said schemes, the 3- and 4-substituted phthalonitriles were prepared starting from nitrophthalonitriles which were reacted with an appropriate alcohol in DMSO, in the presence of potassium carbonate, for 2–72 hours.

The 4,5-disubstituted phthalonitriles are obtained starting from 4,5-dichloro phthalonitrile in a similar way.

The 3,6-disubstituted phthalonitriles are obtained by reaction of the corresponding 2,3-dicyanohydroquinones with an appropriate chloro-, bromo-, tosyl-, or mesyl-derivative (R$_5$Q, where Q is Cl, Br, tosyl or mesyl), in the presence of a base, solvents, and appropriate temperatures according to the particular case.

The present invention also comprises products of formula (I) as defined above, conjugated to a macromolecular carrier to improve the pharmacological characteristics of the latter.

The carrier is normally chosen in the group consisting of amino acids, polypeptides, proteins, and polysaccharides.

The phthalocyanine (I)/carrier bond may occur between the corresponding carboxyl or amine groups or by exploiting other known functional and reactive groups, whether homo- or hetero-bifunctional.

In order to provide a better illustration of the invention, a number of specific examples are given of the synthesis of products of formula (I) and formula (II).

In the formulas that follow, the definitions of a1, a2, a3 and a4 are as indicated below:

a1: Zn-phthalocyanine tetrasubstituted in 2(3), 9(10), 16(17), 23(24);

a2: Zn-phthalocyanine tetrasubstituted in 1(4), 8(11), 15(18), 22(25);

a3: Zn-phthalocyanine octasubstituted in 1, 4, 8, 11, 15, 18, 22, 25;

a4: Zn-phthalocyanine octasubstituted in 2, 3, 9, 10, 16, 17, 23, 24.

EXAMPLE 1
Synthesis of the Compound (II) in which $OR_5$=1-methylpiperidinyl-4-oxy (see Scheme 1)

0.173 g of 3-nitrophthalonitrile (1 mmol) are solubilized in 2 ml of DMSO; to the solution are added 0.173 g of 4-hydroxy-N-methyl piperidine (1.5 mmol) and 1.24 g of $K_2CO_3$. The product is reacted under stirring at room temperature for 72 hours. The solution is filtered, the solvent removed, and the crude reaction product is purified by column chromatography, eluting with a mixture of ethyl acetate (6)/methanol (1)/triethylamine (10), yield, 50%; MW: 241.31.

EXAMPLE 2
Synthesis of the Compound (I) a2 in which R=1-methylpiperidinyl-4-oxy: $R_1$=H (Compound 1)

0.060 g of the compound (II), prepared according to Example 1 (0.25 mmol), are solubilized in 3 mL of n-pentanol in presence of lithium in excess. The mixture is heated while stirring under inert gas up to 150° C. for 15 minutes. The resulting lithium phthalocyanine is transformed into the corresponding metal-free compound by treatment with acids (AcOH: pH of 4-5). Then the green solid is stirred with $Zn(OAc)_2$ in DMF at 80° C. for 20 hours. Formula: $C_{56}H_{60}N_{12}O_4Zn$; light blue solid; MW, 1030.56; UV-vis $\lambda_{max}$ (DMF) 701, 632, 380 nm.

EXAMPLE 3
Synthesis of the Compound (II) in which $OR_5$=2-(piperidin-1-yl)ethoxy (see Scheme 1)

The procedure according to Example 1, starts from 0.089 g of 4-nitrophthalonitrile (0.51 mmol), 0.1 g of N-(2-hydroxyethyl)-piperidine (0.77 mmol) and 0.515 g of $K_2CO_3$ (3.69 mmol). The reaction is stopped after 24 hours by adding water and extracting the product with $CH_2Cl_2$. The organic extracts are dried on $Na_2SO_4$, evaporated to obtain a solid, which is purified by column chromatography (Silica gel; ethyl acetate 4/methanol 1). In this way, 0.1 g of yellowish solid product is obtained (yield 78%).

EXAMPLE 4
Synthesis of the Compound (I) a1 in which R=2-(piperidin-1-yl)ethoxy: $R_1$=H (Compound 2)

0.228 g of the compound (II), prepared according to Example 3 (0.89 mmol), are reacted with $Zn(OAc)_2$ in the presence of 1,8-diazabicyclo[5,4,0]undec-7-ene (DBU) under inert gas at 160° C. for 4 hours. The crude reaction product is purified by extraction with solvents (water/chloroform distribution) and by chromatography (70% yield). Formula: $C_{60}H_{68}N_{12}O_4Zn$; green solid; UV-vis $\lambda_{max}$ (THF) ($\epsilon$) 679 (140320), 612, 354 nm; EAS m/z 1085.6 $(M+H)^+$.

Following a similar procedure, the following products were obtained:

Product (I) a1 in which R=2-(morpholin-4-yl)ethoxy; $R_1$=H (Compound 3)

Formula: $C_{56}H_{60}N_{12}O_8Zn$; blue-green solid; UV-vis $\lambda_{max}$ (DMF) 680, 612, 354 nm;

UV-vis $\lambda_{max}$ (THF) ($\epsilon$) 675 (159410); EAS m/z 1093.8 $(M+H)^+$.

Product (I) a3 in which $R=R_1$=2-[2-(2-hydroxyethoxy)ethoxy]ethoxy (Compound 4)

Formula: $C_{80}H_{112}N_8O_{32}Zn$; green solid; UV-vis $\lambda_{max}$ (DMF) 728, 656, 324 nm; EAS m/z 1761.0 $(M+H)^+$.

Product (I) a2 in which R=2-(piperidin-1-yl)ethoxy; $R_1$=H (Compound 5)

Formula: $C_{60}H_{68}N_{12}O_4Zn$; green-blue solid; UV-vis $\lambda_{max}$ (DMF) ($\epsilon$) 760, 699 (80500), 629, 391 nm; EAS m/z 1085.6 $(M+H)^+$.

Product (I) a1 in which R=(18-crown-6)methoxy; $R_1$=H (Compound 6)

Formula: $C_{84}H_{112}N_8O_{28}Zn$; green solid; UV-vis $\lambda_{max}$ (DMF) ($\epsilon$) 679 (85910), 611, 356 nm; EAS m/z 1746 $(M+H)^+$.

Product (I) a1 in which R=4-(hydroxymethyl)phenoxy; $R_1$=H (Compound 7)

Formula: $C_{60}H_{40}N_8O_8Zn$; green solid; UV-vis $\lambda_{max}$ (DMF) ($\epsilon$) 679 (82970), 611, 356 nm; EAS m/z 1064.1 $(M+H)^+$.

Product (I) a1 in which R=4-(diethylphosphonylmethyl)phenoxy; $R_1$=H (Compound 8)

Formula: $C_{76}H_{76}N_8O_{20}P_4Zn$; green solid; UV-vis $\lambda_{max}$ (DMF) 678, 610, 357 nm.

Product of formula (I) a3 in which $R=R_1$=2-[2-(2-diethylphosphonylethoxy)ethoxy]ethoxy (Compound 9)

Formula: $C_{112}H_{184}N_8O_5P_8Zn$; green solid; UV-vis $\lambda_{max}$ (DMF) 733, 661, 360 nm.

Product (I) a3 in which $R=R_1$=2-(morpholin-4-yl)ethoxy (Compound 10)

Formula: $C_{80}H_{104}N_{16}O_{16}Zn$; brownish-green solid; UV-vis $\lambda_{max}$ (DMF) 736, 661, 349 nm.

Product (I) a3 in which $R=R_1$=3-(piperidin-1-yl)propoxy (Compound 11)

Formula: $C_{96}H_{136}N_{16}O_8Zn$; green solid; UV-vis $\lambda_{max}$ (DMF) 818, 742, 666, 350 nm.

Product (I) a1 in which R=2-(pirrolidin-2-one-1-yl)ethoxy; $R_1$=H (Compound 12)

Formula: $C_{56}H_{52}N_{12}O_8Zn$; blue solid; UV-vis $\lambda_{max}$ (DMF) ($\epsilon$) 680 (104100), 611, 354 nm; EAS m/z 1085.2 $(M+H)^+$.

Product (I) a1 in which R=2-{2-[2-(2-hydroxyethoxy)ethoxy]ethoxy}ethoxy; $R_1$=H (Compound 13)

Formula: $C_{64}H_{80}N_8O_{20}Zn$; blue-green solid; UV-vis $\lambda_{max}$ (DMF) ($\epsilon$) 680 (133120), 679, 611, 355 nm.

Product (I) a2 in which R=2-(morpholin4-yl)ethoxy; $R_1$=H (Compound 14)

Formula: $C_{56}H_{60}N_{12}O_8Zn$; green solid; UV-vis $\lambda_{max}$ (DMF) ($\epsilon$) 698 (125910), 628, 322 nm; EAS m/z 1094.1 $(M+H)^+$.

Product (I) a1 in which R=1-methylpiperidinyl-4-oxy; $R_1$=H (Compound 15)

Formula: $C_{56}H_{60}N_{12}O_4Zn$; blue solid; UV-vis $\lambda_{max}$ (DMF) 681, 613, 354 nm.

Product (I) a2 in which R=(1-methylpiperidin-2-yl)methoxy; $R_1$=H (Compound 16) Formula:

$C_{60}H_{68}N_{12}O_4Zn$; brownish-green solid; UV-vis $\lambda_{max}$ (DMF) 715, 642, 318 nm.

Product (I) a2 in which R=2-{4-[1-(2-sulfoethyl)] piperazinyl}ethoxy; $R_1$=H (Compound 17) Formula: $C_{64}H_{80}N_{16}O_{16}S_4Zn$; blue-green solid; UV-vis $\lambda_{max}$ (DMF) 701, 631, 322 nm.

Product (I) a1 in which R=2-{4-[1-(2-sulfoethyl)] piperazinyl}ethoxy; $R_1$=H (Compound 18) Formula: $C_{64}H_{80}N_{16}O_{16}S_4Zn$; blue-green solid; UV-vis $\lambda_{max}$ (DMF) 680, 612, 354 nm.

Product of formula (I) a1 in which R=1,3-bis-(dimethylamino)propyl-2-oxy; $R_1$=H (Compound 19) Formula: $C_{60}H_{80}N_{16}O_4Zn$; blue-green solid.

Product (I) a1 in which R=pyrimidinyl-2-oxy; $R_1$=H (Compound 20)
Formula: $C_{48}H_{24}N_{16}O_4Zn$; blue-green solid.

Product (I) a1 in which R=pyridinyl-2-oxy; $R_1$=H (Compound 21)
Formula: $C_{52}H_{28}N_{12}O_4Zn$; blue-green solid.

Product (I) a1 in which R=3-(dimethylamino)phenoxy; $R_1$=H (Compound 22)
Formula: $C_{64}H_{52}N_{12}O_4Zn$; blue-green solid.

Product (I) a1 in which R=pyridinyl-4-oxy; $R_1$=H (Compound 23)
Formula: $C_{52}H_{28}N_{12}O_4Zn$; blue-green solid.

Product (I) a1 in which R=(pyridin4-yl)methoxy; $R_1$=H (Compound 24)
Formula: $C_{56}H_{36}N_{12}O_4Zn$; blue-green solid.

Product (I) a3 in which R=$R_1$=4-(diethylamino)phenoxy (Compound 25)
Formula: $C_{112}H_{120}N_{16}O_8Zn$; blue-green solid.

Product (I) a1 in which R=3-(diethylamino)phenoxy; $R_1$=H (Compound 26)
Formula: $C_{72}H_{68}N_{12}O_4Zn$; blue-green solid.

Product (I) a4 in which R=$R_1$=3-(dimethylamino)phenoxy (Compound 27)
Formula: $C_{96}H_{88}N_{16}O_8Zn$; blue-green solid.

Product (I) a2 in which R=3-(dimethylamino)phenoxy; $R_1$=H (Compound 28)
Formula: $C_{64}H_{52}N_{12}O_4Zn$; blue-green solid.

Product (I) a2 in which R=3-(diethylamino)phenoxy; $R_1$=H (Compound 29)
Formula: $C_{72}H_{68}N_{12}O_4Zn$; blue-green solid.

Product (I) a4 in which R=R'=3-(diethylamino)phenoxy (Compound 30)
Formula: $C_{112}H_{120}N_{16}O_8Zn$; blue-green solid.

EXAMPLE 5

Synthesis of the Compound (II) in which $OR_5$=2-(hydroxy)ethoxy (see Scheme 3)

0.32 g of 2,3-dicyanohydroquinone (2 mmol) are suspended in 5 mL of xylene, and 1.0 g of 2-bromoethanol (8 mmol) and 1.0 g of triethylamine (1.37 mL; 10 mmol) are added to the suspension. The product is heated under stirring at 130° C. for 24 hours then the xylene is decanted. The residue is then treated with methanol to obtain 0.24 g of white-grey solid (yield, 70%).

MW, 203.19; $^1$H NMR (DMSO-$d_6$) δ 7.65 (s, 2H), 4.95 (t, 2H), 4.20 (t, 4H), 3.80 (m, 4H).

EXAMPLE 6

Synthesis of the Compound (I) a3 in which R=$R_1$=2-(hydroxy)ethoxy (Compound 5 0.1 g of the compound (II), prepared according to Example 5 (0.5 mmol), is solubilized in N,N-dimethylethanolamine, ammonia is passed through this solution for 15 minutes at room temperature then the temperature is raised to 140–160° C. for 6 hours, continuing the stream of ammonia. The desired product is obtained by flash-chromatography purification on Silica gel in a 25% yield. Formula: $C_{48}H_{48}N_8O_{16}Zn$; green solid; UV-vis $\lambda_{max}$ (DMF) 741, 666, 357 nm; EAS m/z 1056.8 (M+H)$^+$.

EXAMPLE 7

Synthesis of the Compound (I) a1 in which R=N-(2-aminoethyl)benzamidoyl-4-oxy trifluoro acetate: $R_1$=H (Compound 32)

a) Functionalization of the polystirene-based resin with the phthtalodinitrile 0.159 g (0.078 mmol) of diaminoethane-trityl resin (0.49 mmol/g) are swelled in 12.5 mL of DMF. To this suspension 0.282 g (0.78 mmol) of the succinimide ester of the compound (II) in which $R_5$=4-carboxyphenyl are added, and the product is kept under stirring at room temperature for 18 hours. The liquid phase is removed from the resin by vacuum filtration, and the resin is washed several times with small volumes of DMF, $CH_2Cl_2$ and MeOH.

b) Solid-phase condensation reaction

The obtained functionalized resin (0.078 mmol) is swelled in 2 mL of DMF for one hour at 50° C. 0.080 g (0.43 mmol) of zinc(ll)acetate and 0.322 mL (2.15 mmol) of DBU are added and the suspension is heated up to 160° C. for 4 hours, under stirring and nitrogen. After cooling at room temperature, the two phases are separated by vacuum filtration, and the solid phase is washed with MeOH and DMF.

c) Separation of the Zn-phthalocyanine from the resin

The green-blue resin is suspended in a solution of trifluoroacetic acid (TFA) (5%) and tri-isopropyl silane (TIS) (5%) in $CH_2Cl_2$ and kept in this solution for 1.5 hours. The two phases are then separated by vacuum filtration and the resin is washed with $CH_2Cl_2$. The solid phase is treated with small volumes of DMF and MeOH alternatively until the solution is colourless. The product is obtained by concentration of the filtrate in a 60% yield. Formula: $C_{68}H_{56}N_{16}O_8Zn$ $(CF_3COOH)_4$; UV-vis $\lambda_{max}$ (DMF) 676, 609, 349 nm.

Using procedures known in the literature, the following products were obtained:

Product (I) a1 in which R=2-(morpholin-4-yl)ethoxy methylammonium iodide; $R_1$=H (Compound 33) Formula: $C_{60}H_{72}I_4N_{12}O_8Zn$; blue-green solid; UV-vis $\lambda_{max}$ (DMF) (ε) 677 (167330).

Product (I) a1 in which R=2-(piperidin-1-yl)ethoxy methylammonium iodide; $R_1$=H (Compound 34) Formula: $C_{64}H_{80}I_4N_{12}O_4Zn$; blue solid; UV-vis $\lambda_{max}$ (DMF) (ε) 678 (144840), 611, 353 nm.

Product (I) a2 in which R=2-(piperidin-1-yl)ethoxy methylammonium iodide; $R_1$=H (Compound 35) Formula: $C_{64}H_{80}I_4N_{12}O_4Zn$; green solid; UV-vis $\lambda_{max}$ (DMF) 753, 701, 731 nm.

Product (I) a2 in which R=2-(morpholin-4-yl)ethoxy methylammonium iodide; $R_1$=H (Compound 36) Formula: $C_{60}H_{72}I_4N_{12}O_8Zn$; green solid.

Product (I) a3 in which R=$R_1$=2-(morpholin-4-yl)ethoxy methylammonium iodide (Compound 37) Formula: $C_{88}H_{128}I_8N_{16}O_{16}Zn$; green solid.

Product (I) a1 in which R=1-methylpiperidinyl-4-oxy metilammonium iodide; $R_1$=H (Compound 38) Formula: $C_{60}H_{72}I_4N_{12}O_4Zn$; green solid.

Product (I) a3 in which R=$R_1$=3-(piperidin-1-yl)propoxy metilammonium iodide (Compound 39) Formula: $C_{100}H_{152}I_8N_{16}O_8Zn$; green solid.

Product (I) a1 in which R=1,3-bis-(dimethylamino)propyl-2-oxy dimethylammonium iodide; $R_1$=H (Compound 40) Formula: $C_{68}H_{104}I_8N_{16}O_4Zn$; blue-green solid.

Product (I) a1 in which R=piridinyl-2-oxy methylammonium iodide; $R_1$=H (Compound 41) Formula: $C_{56}H_{40}I_4N_{12}O_4Zn$; blue-green solid.

Product (I) a1 in which R=3-(dimethylamino)phenoxy methylammonium iodide; $R_1$=H (Compound 42) Formula: $C_{68}H_{64}I_4N_{12}O_4Zn$; blue-green solid.

Product (I) a1 in which R=piridinyl-4-oxy methylammonium iodide; $R_1$=H (Compound 43) Formula: $C_{56}H_{40}I_4N_{12}O_4Zn$; blue-green solid.

Product (I) a1 in which R=(piridin4-yl)methoxy methylammonium iodide; $R_1$=H (Compound 44) Formula: $C_{60}H_{48}I_4N_{12}O_4Zn$; blue-green solid.

Product (I) a3 in which R=$R_1$=4-(diethylamino)phenoxy methylammonium iodide (Compound 45) Formula: $C_{120}H_{144}I_8N_{16}O_8Zn$; green solid.

Product (I) a1 in which R=3-(diethylamino)phenoxy methylammonium iodide; $R_1$=H (Compound 46) Formula: $C_{76}H_{80}I_4N_{12}O_4Zn$; green solid.

Product (I) a4 in which R=$R_1$=3-(dimethylamino)phenoxy methylammonium iodide (Compound 47) Formula: $C_{104}H_{114}I_8N_{16}O_8Zn$; green solid.

Product (I) a4 in which R=$R_1$=3-(diethylamino)phenoxy methylammonium iodide (Compound 48) Formula: $C_{112}H_{144}I_8N_{16}O_8Zn$; green solid.

Product (I) a4 in which R=$R_1$=3-(diethylamino)phenoxy ethylammonium iodide (Compound 49) Formula: $C_{128}H_{160}I_8N_{16}O_8Zn$; green solid.

Product (I) a2 in which R=3-(diethylamino)phenoxy methylammonium iodide; $R_1$=H (Compound 50) Formula: $C_{76}H_{80}I_4N_{12}O_4Zn$; green solid.

Product (I) a1 in which R=3-(diethylamino)phenoxy ethylammonium iodide; $R_1$=H (Compound 51) Formula: $C_{80}H_{88}I_4N_{12}O_4Zn$; green solid.

Product (I) a2 in which R=3-(diethylamino)phenoxy ethylammonium iodide; $R_1$=H (Compound 52) Formula: $C_{80}H_{88}I_4N_{12}O_4Zn$; green solid.

Product (I) a2 in which R=3-(dimethylamino)phenoxy methylammonium iodide; $R_1$=H (Compound 53)Formula: $C_{68}H_{64}I_4N_{12}O_4Zn$; green solid.

EXAMPLE 8

General Synthesis of Amine or Carboxylic Derivative of Formula (I) Bound to Polypeptides 200 μL of a 5 mg/ml solution of bovine serum albumin (BSA) in PBS (pH: 8.5) containing 25 equiv. of I added as solution in DMSO is incubated for 10 minutes at room temperature. 25 equiv. of a water soluble carbodiimide are added slowly to the sample refrigerated at 4° C. and the reaction mixture is gently stirred for 30 minutes, while the temperature reaches room temperature.

The conjugation product is purified by gel filtration (Sephadex G25) eluting with PBS pH: 7.2, and collecting the fractions containing the conjugate, which are visible owing to the green-blue colour, and from which the solid product is obtained by liophilization.

The protein concentration and the number of moles of the Compound (I) introduced per mole of BSA (labelling ratio) may be determined spectrophotometrically and it was found to range from 3.5 to 10 moles of phthalocyanine per mole of BSA.

Pharmaceutical Formulations

Therapeutic compositions containing the compounds of the present invention include liposomes or microcapsules, dispersions, solutions for parenteral injection, preparations for topical application, etc.

The topical formulations according to the invention are, for example, lotions, creams, ointments or gels.

Particularly preferred are DMSO or Azone aqueous solutions, up to 50 wt %.

The compounds of the present invention having lipophilic characteristics may be incorporated in liposomes or microcapsules and used in this form for both types of application mentioned above.

The photodynamic therapy that uses the compounds of the present invention affords numerous advantages.

They are not toxic in the absence of light, and hence in the non-excited state.

Each molecule may be repeatedly excited, with the consequent production of singlet oxygen or other reactive species, which entails lethal effects for the cells.

Given their short average life time they hit the target cell without possibility of affecting vicinal cells.

The photodynamic therapy that uses the present compounds is thus selective and non-toxic, in that the singlet oxygen produced that does not react with biological targets undergoes a rapid decay ; in fact, the production of oxygen takes place immediately after irradiation and stops as soon as irradiation is interrupted.

The dosages normally range from 0.1 to 20 mg of compound of formula (I) per kilogram of body weight, preferably 0.2–5 mg/kg of body weight.

The appropriate light sources required to carry out PDT are well known to the art and may, for instance, be white light associated to suitable filters or laser light having the specific wavelength required, with wavelengths between 600 and 950 nm, preferably 650–750 nm.

The total applied amount of radiation varies according to the treatment and the location of the tissues to be treated.

Generally the amount of radiation is between 50–1000 $J/cm^2$, preferably between 100 and 350 $J/cm^2$.

BIOCIDAL ACTIVITY

The compounds synthesized have been assayed for their antifungal and antibacterial (Gram-positive and Gram-negative) activity. For the experiments the following microorganisms were used: *Candida albicans* (yeast), *Staphylococcus aureus* (Gram-positive) and *Pseudomonas aeruginosa*, as well as *E.coli, Porphyromonas gengivalis, Branhamella catarralis* (Gram-negative).

All the micro-organisms were used in the experiments in a stationary state of growth. The experimental protocol was the following:

Dilution of the cell suspension in the range $10^6 \div 10^9$ UFC/mL in the appropriate medium. Addition of an aliquot of stock solution of the compound to be tested to the cell suspension up to the intended final concentrations. Incubation in dark at 37° C. (5 min to 1 hour). Irradiation ($625 \leq \lambda \leq 850$ nm; $10 \div 100$ mW/$cm^2$; $1 \div 30$ min) of cell suspension for each dilution of photosensitizing agent. Taking the exposed samples at the time intervals given in the tables, plating and incubating at 37° C. in the appropriate colture medium for the specific microorganism, for the colonies to be counted.

As an example, photoinactivation of some Gram-positive and negative microorganisms by using some compounds of the present invention are given in TABLE A.

Diagram 1 shows the variation of colony forming units (CFU) as a function of administered light dose, while Diagram 2 shows the cell survival (in %) as a function of the photosensitizer concentration.

As an example the usefulness of derivatives (I) in the treatment of cell iperproliferation and psoriasis is demonstrated in Tables B and C where it is shown the in vivo erhithemal effect produced by compounds 15 and 42 and the skin recovery after treatment within 10 days. This finding thus support the possibility to use such compounds for the elimination of epidermal cells responsible for the occurrence of the above mentioned patologies.

The pharmacokinetic of compound 15 reported in Table D, still as an example, demonstrates the selective photosensitizer uptake by epidermal cells and neither appreciable systemic absorption nor localization in tissues other than skin. Compounds are almost totally eliminated from the application site within 3 hours. Finally, Table E gives the difference in the *E.coli* survival as post irradiation times by using compound 40 in comparison with a previously described phtalocyanine derivative, while Table F accounts for the high affinity of compounds 40 and 42 on *Staphylococcus aureus*, *E.Coli* and *Branhamella catarralis*, evaluated as percentage of bound compound after incubation followed from up to three washing steps.

TABLE A

Photoinactivation of microorganisms
*Staphylococcus aureus* (ATCC 6538P)

| Compound | Concentration ($\mu$M) | mW/cm2 (min.) | Cell mortality |
|---|---|---|---|
| 3 | 0.6 | 15(30) | 99.00 |
| 2 | 0.5 | 15(30) | 99.99 |
| 6 | 0.6 | 15(30) | 99.99 |
| ZnPC | 1 | 15(30) | 99.99 |
| 40 | 1 | 100(1) | 99.999 |
| 42 | 1 | 100(1) | 99.9998 |

ZnPC (Commercial Zn-Phthalocyanine)

*Pseudomonas aeruginosa* (ATCC 9027)

| Compound | Concentration ($\mu$M) | mW/cm$^2$ (min) | Cell mortality |
|---|---|---|---|
| 33 | 28 | 18 (30) | 37 |
| 34 | 8 | 18 (30) | 21 |

*E. Coli* (strain 04)

| Compound | Concentration ($\mu$M) | mW/cm$^2$ (min) | Cell mortality |
|---|---|---|---|
| 40 | 1 | 100 (1) | 99.9999 |

ZnPC was found not active

*Branhamella catarrhalis*

| Compound | Concentration ($\mu$M) | mW/cm$^2$ (min) | Cell mortality |
|---|---|---|---|
| 40 | 1 | 100 (1) | 99.9999 |
| 42 | 1 | 100 (1) | 99.98 |
| 40 | 0.5 | 100 (1) | 99.99 |
| 42 | 0.5 | 100 (1) | 99.75 |

ZnPC was found not active

TABLE B

Laser irradiation after topical application of
Compound 15 (water/5% DMSO)

| Hours after irradiation | I | II | III | IV | V |
|---|---|---|---|---|---|
| 24 h | +++ and edema in all area | +++ and edema in all area | +++ and edema in all area | +++ and edema in all area | +++ and edema in all area |
| 48 h | *+++ | *+++ | *+++ | *+++ | *+++ |
| 73 h | *+++ | *+++ | *+++ | *+++ | *+++ |
| 4 days | +++ | +++ | +++ | +++ | +++ |
| 5 days | ++ | +++ | +++ | ++ | +++ |
| 7 days | ++ | ++ | ++ | + | ++ |
| 10 days | + | + | ++ | + | + |

TABLE C

Laser irradiation after topical application of
Compound 42 (water/5% DMSO)

| Hours after irradiation | I | II | III | IV | V |
|---|---|---|---|---|---|
| 24 h | ++ | ++ | ++ | +++ | ++ |
| 48 h | +++ | +++ | +++ and edema surrounding all area | +++ | +++ |
| 73 h | +++ | +++ | +++ and edema surrounding all area | +++ | +++ |
| 4 days | +++ | +++ | +++ and edema surrounding all area | +++ | +++ |
| 5 days | +++ | ++ | +++ | +++ | ++ |
| 6 days | ++ | + | +++ | +++ | + |
| 7 days | +/− | +/− | +++ | ++ | +/− |
| 8 days | + | 0 | ++ | ++ | 0 |
| 10 days | +/− | − | +/− | + | 0 |

I, II, III, IV, V indicate the number of experiments.

Experimental conditions: Fluence rate 150 mW/cm$^2$ for 13.3 min (Total energy 120 J)

At the 10$^{th}$ day animals were sacrificed

Legend:

− no response 0 weak response (erythema and or edema)

+/− superficial eschar on part of treated area

+ superficial eschar on all the area

++ deep eschar on part of the area

+++ deep eschar covering all the area

*+++ very deep eschar

TABLE D

Pharmacokinetics of Compound 15 topically administered
(20 $\mu$g/cm$^2$, water/5% DMSO)

| | I | II | III | Average accumulation (%) |
|---|---|---|---|---|
| Serum 1 h | 0 | 0 | 0 | 0 |
| Skin 1 h | 1547.64 ng/cm$^2$ | 2278.60 ng/cm$^2$ | 2330.00 ng/cm$^2$ | 10.23 |
| Liver 1 h | 0 | 0 | 0 | 0 |
| Serum 3 h | 0 | 0 | 0 | 0 |
| Skin 3 h | 593 ng/cm$^2$ | 690 ng/cm$^2$ | 562 ng/cm$^2$ | 0.03 |
| Liver 3 h | 0 | 0 | 0 | 0 |

I, II, III indicate the number of experiments.

TABLE E

Survival of *Escherichia coli* (strain 04) irradiated for 1 min at a fluence rate of 100 mW/cm$^2$ with a diode laser (675 nm) after 1 min incubation with different photosensitizers

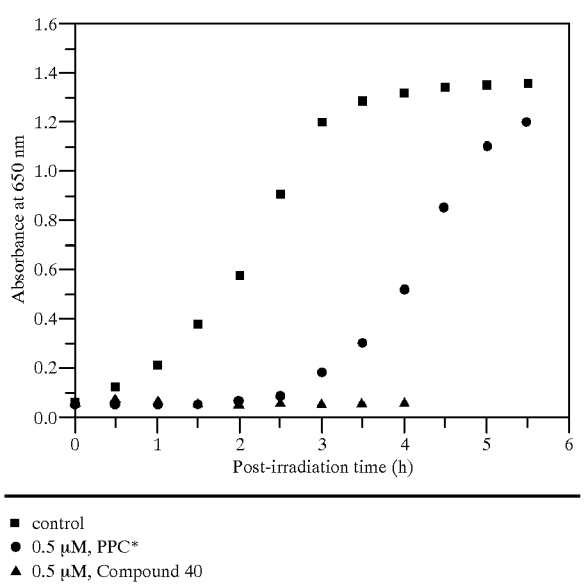

- control
- 0.5 μM, PPC*
- 0.5 μM, Compound 40

*PPC: reported by A. Minnock et al. J. Photochem. Photobiol. 32: 159–164, (1996).

TABLE F

Recovery of Compound 40 and Compound 42 (nmoles/mg of cell protein) bound to *Staphylococcus aureus*, *Escherichia coli*, *Branhamella catarralis* after 5 min. of incubation and washing.

| Microorganism | Compound N° (conc. μM) | Recovery of phthalocyanine (nmoles/mg of cell protein) after the following washing steps | | |
|---|---|---|---|---|
| | | 0 | 1 | 3 |
| *Staphylococcus aureus* | 40 (5 μM) | 100% | 82% | 56% |
| | 42 (5 μM) | 100% | 100% | 84% |
| *Escherichia coli* | 40 (10 μM) | 100% | 56% | 32.4% |
| | 42 (10 μM) | 100% | 72% | 52% |
| *Branhamella catarralis* | 40 (5 μM) | 100% | 70% | 67% |
| | 42 (5 μM) | 100% | 92% | 90% |

SCHEME 1

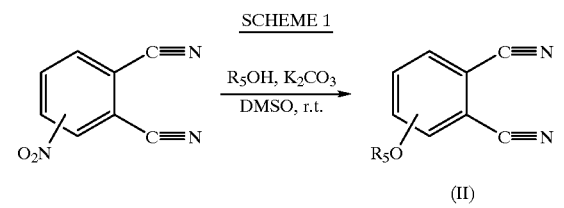

SCHEME 2

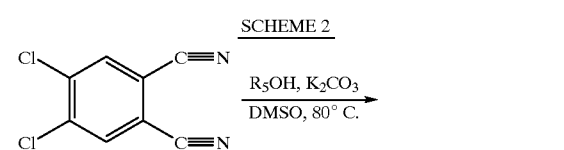

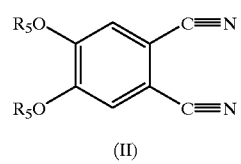

SCHEME 3

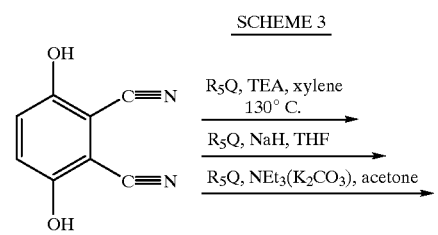

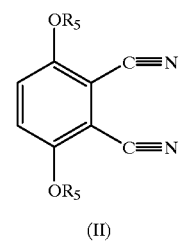

SCHEME 4

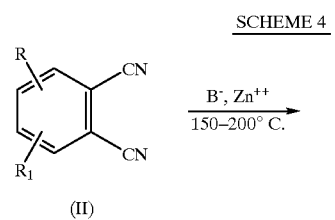

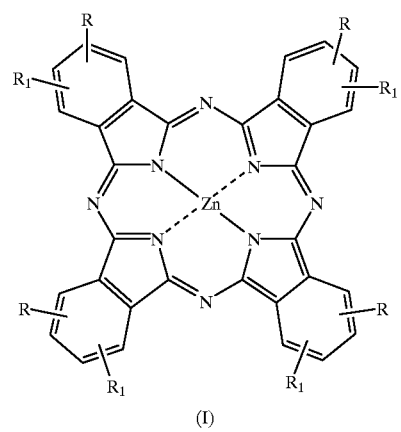

We claim:
1. Compounds of general formula (I)

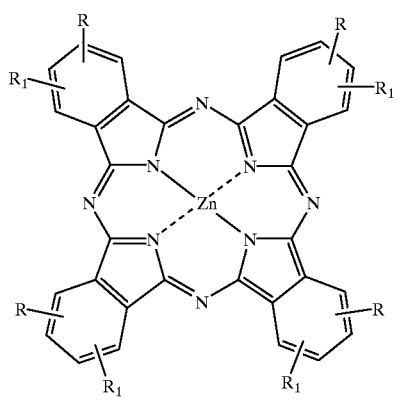

in which:

R and R₁ represent H or the group X-R₅, where:
X is chosen in the group consisting of —CH₂—, O, N, S, C=O, and

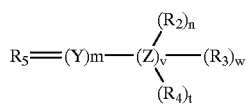

where:
Y is chosen in the group consisting of $C_{1-10}$-alkyl, phenyl possibly substituted, $(CH_2CH_2O)_p$, where p ranges from 1 to 4;
Z is chosen in the group consisting of H, N, O, S, SO₃, —CH—, —CH₂— carbon atom, CH₂O, CONH, $(CH_2)_qCO_2$, where q ranges from 0 to 2;
R₂ is chosen in the group consisting of H, $C_{1-12}$-alkyl, PO(OEt)₂, CH₂CH₂NH₂, aryl, and crown ether, or it forms, with the Z group to which it is bound, a saturated or unsaturated heterocycle, possibly substituted, which may contain up to two hetero-atoms chosen among N, O, and S;
R₃ and R₄, which may be the same or different from one another, are chosen in the group consisting of H, CH₃, and C₂H₅, $C_{3-12}$ alkyl m, n, w, t (independently from one another) are 0 or 1;
V is an integer comprised between 1 and 5;
with the proviso that at least one of R and R₁ is always other than H.

2. Compounds according to claim 1, in which the saturated or unsaturated heterocycle possibly substituted is chosen in the group consisting of morpholine, piperidine, pyridine, pyrimidine, piperazine, pyrrolidine, and pyrroline.

3. Compounds according to claim 2, in which the group X-R₅ is chosen in the group consisting of:

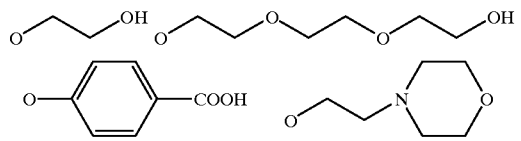

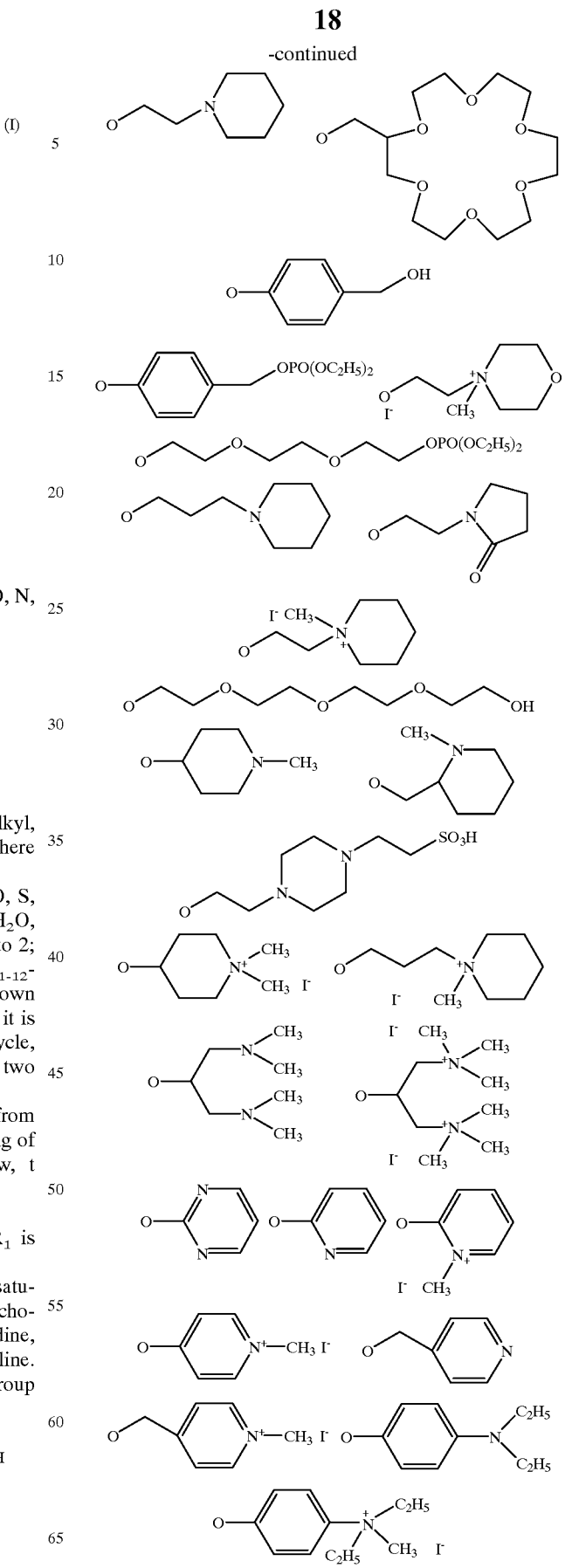

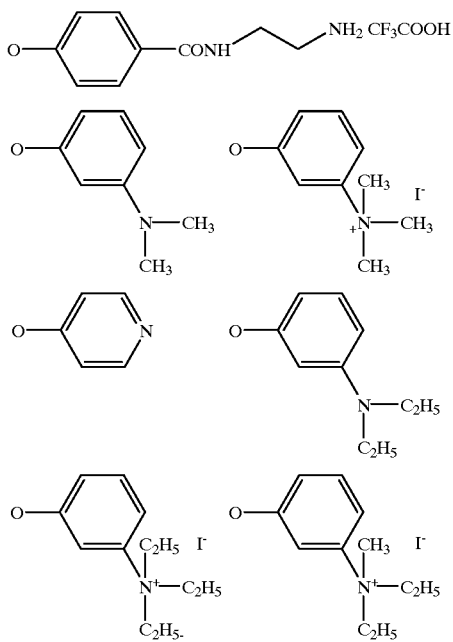

4. Compounds according to claim 3, in which the group X-R$_5$ contains tertiary or quaternary nitrogen.

5. Compounds of general formula (I) according to claim 1, in which the products are defined by the following formulas:

(I) a2 in which R=1-methylpiperidinyl-4-oxy; R$_1$=H
(I) a1 in which R=2-(piperidin-1-yl)ethoxy; R$_1$=H
(I) a1 in which R=2-(morpholin-4-yl)ethoxy; R$_1$=H
(I) a3 in which R=R$_1$=2-[2-(2-hydroxyethoxy)ethoxy]ethoxy
(I) a2 in which R=2-(piperidin-1-yl)ethoxy; R$_1$=H
(I) a1 in which R=(18-crown-6)methoxy; R$_1$=H
(I) a1 in which R=4-(hydroxymethyl)phenoxy; R$_1$=H
(I) a1 in which R=4-(diethylphosphonylmethyl)phenoxy; R$_1$=H
(I) a3 in which R=R$_1$=2-[2-(2-diethylphosphonylethoxy)ethoxy]ethoxy
(I) a3 in which R=R$_1$=2-(morpholin-4-yl)ethoxy
(I) a3 in which R=R$_1$=3-(piperidin-1-yl)propoxy
(I) a1 in which R=2-(2-oxopirrolidin-1-yl)ethoxy; R$_1$=H
(I) a1 in which R=2-{2-[2-(2-hydroxyethoxy)ethoxy]ethoxy}ethoxy; R$_1$=H
(I) a2 in which R=2-(morpholin-4-yl)ethoxy; R$_1$=H
(I) a1 in which R=1-methylpiperidinyl-4-oxy; R$_1$=H
(I) a2 in which R=(1-methylpiperidin-2-yl)methoxy; R$_1$=H
(I) a2 in which R=2-{4-[1-(2-sulfoethyl)]piperazinyl}ethoxy; R$_1$=H
(i) a1 in which R=2-{4-[1-(2-sulfoethyl)]piperazinyl}ethoxy; R$_1$=H
(I) a1 in which R=1,3-bis-(dimethylamino)propyl-2-oxy; R$_1$=H
(I) a1 in which R=pyrimidinyl-2-oxy; R$_1$=H
(I) a1 in which R=pyridinyl-2-oxy; R$_1$=H
(I) a1 in which R=3-(dimethylamino)phenoxy; R$_1$=H
(I) a1 in which R=pyridinyl-4-oxy; R$_1$=H
(I) a1 in which R=(pyridin-4-yl)methoxy; R$_1$=H
(I) a3 in which R=R$_1$=4-(diethylamino)phenoxy
(I) a1 in which R=3-(diethylamino)phenoxy; R$_1$=H
(I) a4 in which R=R$_1$=3-(dimethylamino)phenoxy
(I) a2 in which R=3-(dimethylamino)phenoxy; R$_1$=H
(I) a2 in which R=3-(diethylamino)phenoxy; R$_1$=H
(I) a4 in which R=R$_1$=3-(diethylamino)phenoxy
(I) a3 in which R=R$_1$=2-(hydroxy)ethoxy
(I) a1 in which R=N-(2-aminoethyl)benzamidoyl-4-oxy trifluoro acetate; R$_1$=H
(I) a1 in which R=2-(morpholin4-yl)ethoxy methylammonium iodide; R$_1$=H
(I) a1 in which R=2-(piperidin-1-yl)ethoxy methylammonium iodide; R$_1$=H
(I) a2 in which R=2-(piperidin-1-yl)ethoxy methylammonium iodide; R$_1$=H
(I) a2 in which R=2-(morpholin-4-yl)ethoxy methylammonium iodide; R$_1$=H
(I) a3 in which R=R$_1$=2-(morpholin-4-yl)ethoxy methylammonium iodide
(I) a1 in which R=1-methylpiperidinyl-4-oxy metilammonium iodide; R$_1$=H
(I) a3 in which R=R$_1$=3-(piperidin-1-yl)propoxy metilammonium iodide
(I) a1 in which R=1,3-bis-(dimethylamino)propyl-2-oxy dimethylammonium iodide; R$_1$=H
(I) a1 in which R=piridinyl-2-oxy methylammonium iodide; R$_1$=H
(I) a1 in which R=3-(dimethylaminoyphenoxy methylammonium iodide; R$_1$=H
(I) a1 in which R=piridinyl-4-oxy methylammonium iodide; R$_1$=H
(I) a1 in which R=(piridin-4-yl)methoxy methylammonium iodide; R$_1$=H
(I) a3 in which R=R$_1$=4-(diethylamino)phenoxy methylammonium iodide
(I) a1 in which R=3-(diethylamino)phenoxy methylammonium iodide; R$_1$=H
(I) a4 in which R=R$_1$=3-(dimethylamino)phenoxy methylammonium iodide
(I) a4 in which R=R$_1$=3-(diethylamino)phenoxy methylammonium iodide
(I) a4 in which R=R$_1$=3-(diethylamino)phenoxy ethylammonium iodide
(I) a2 in which R=3-(diethylamino)phenoxy methylammonium iodide; R$_1$=H
(I) a1 in which R=3-(diethylamino)phenoxy ethylammonium iodide; R$_1$=H
(I) a2 in which R=3-(diethylamino)phenoxy ethylammonium iodide; R$_1$=H
(I) a2 in which R=3-(dimethylamino)phenoxy methylammonium iodide; R$_1$=H.

6. Conjugates consisting of a compound of general formula (I) according to claim 1 and of a macromolecule chosen in the group consisting of polypeptides, proteins and polysaccharides.

7. Process for the preparation of compounds of formula (I) according to claim 1 wherein the four substituents are identical, in which:
   a) a polystyrene-based resin is used as substrate for attachment of the phthalo dinitrile;

b) the functionalized resin is heated in the presence of Zn (II) salt, with consequent formation of the Zn-phthalocyanine derivative in the solid phase;

c) the Zn-phthalocyanine derivative is cleaved from the resin yielding an impurities free products.

8. A method of treating infectious diseases and diseases characterized by cellular hyperproliferation, said method comprising administering to a host an effective amount of a compound according to claim 1, or mixtures thereof.

9. A method of treating psoriasis, said method comprising administering to a host an effective amount of a compound according to claim 8.

10. A method of treating intimal hyperplasia or benign prostate hyperplasia, said method comprising administering to a host an effective amount of a compound according to claim 8.

11. A method of treating atheromas, said method comprising administering to a host an effective amount of a compound according to claim 8.

12. A method of treating viral, fungal or bacterial pathological conditions, said method comprising administering to a host an effective amount of a compound according to claim 8.

13. A method for the preparation of a diagnostic agent, said method comprising admixing a compound according to claim 6, or mixtures thereof in combination with pharmaceutically acceptable excipients.

14. Pharmaceutical formulation for the treatment of infectious deseases and deseases characterized by cellular hyperproliferation containing a compound according to claim 1, as active principle, possibly in combination with pharmaceutically acceptable excipients.

15. Diagnostic agents containing as active principle a compound according to claim 1 possibly in combination with a pharmaceutically acceptable carrier.

16. A method of treating infectious diseases and diseases characterized by cellular hyperproliferation, said method comprising administering to a host an effective amount of a conjugate according to claim 6.

17. A method of treating psoriasis, said method comprising administering to a host an effective amount of a conjugate according to claim 6.

18. A method of treating intimal hyperplasia or benign prostate hyperplasia, said method comprising administering to a host an effective amount of a conjugate according to claim 6.

19. A method of treating atheromas, said method comprising administering to a host an effective amount of a conjugate according to claim 6.

20. A method of treating viral, fungal or bacterial pathological conditions, said method comprising administering to a host an effective amount of a conjugate according to claim 6.

* * * * *